United States Patent
Dairiki et al.

(10) Patent No.: US 9,901,092 B2
(45) Date of Patent: Feb. 27, 2018

(54) PEST CONTROL AGENT IN FORM OF STABLE SUSPENSION

(75) Inventors: Hiroshi Dairiki, Odawara (JP); Eriko Okada, Fujieda (JP)

(73) Assignee: Nippon Soda Co., Ltd., Tokyo (JP)

( * ) Notice: Subject to any disclaimer, the term of this patent is extended or adjusted under 35 U.S.C. 154(b) by 610 days.

(21) Appl. No.: 12/310,655

(22) PCT Filed: Sep. 10, 2007

(86) PCT No.: PCT/JP2007/067584
§ 371 (c)(1),
(2), (4) Date: Mar. 3, 2009

(87) PCT Pub. No.: WO2008/032671
PCT Pub. Date: Mar. 20, 2008

(65) Prior Publication Data
US 2010/0234436 A1    Sep. 16, 2010

(30) Foreign Application Priority Data
Sep. 12, 2006  (JP) ................................. 2006-246658

(51) Int. Cl.
  *A01N 25/04* (2006.01)
  *A01N 47/44* (2006.01)
  *A01N 43/80* (2006.01)
  *A01N 47/34* (2006.01)

(52) U.S. Cl.
  CPC ............. *A01N 25/04* (2013.01); *A01N 43/80* (2013.01); *A01N 47/34* (2013.01); *A01N 47/44* (2013.01)

(58) Field of Classification Search
  CPC ........ A01N 25/04; A01N 47/34; A01N 47/44; A01N 43/80; A02N 43/80
  USPC .......................................... 424/400; 514/373
  See application file for complete search history.

(56) References Cited

U.S. PATENT DOCUMENTS

| 3,934,002 | A | * | 1/1976 | Haefele ............................ 424/54 |
| 4,256,731 | A | * | 3/1981 | Curtis et al. .................... 424/54 |
| 4,997,471 | A | * | 3/1991 | Mente ............................ 504/360 |
| 5,491,165 | A |   | 2/1996 | Dehne et al. |
| 5,674,521 | A | * | 10/1997 | Gehrke .................. A61K 9/205 424/423 |
| 6,030,923 | A | * | 2/2000 | Okano et al. ................. 504/362 |
| 6,074,987 | A | * | 6/2000 | Shafer .................... A01N 25/04 424/405 |
| 6,113,936 | A | * | 9/2000 | Takebayashi ............ B01J 13/18 424/408 |
| 6,166,058 | A |   | 12/2000 | Mailer et al. |
| 6,407,126 | B1 |   | 6/2002 | Schelberger et al. |
| 6,589,967 | B1 | * | 7/2003 | Sano et al. .................... 514/345 |
| 6,884,754 | B1 | * | 4/2005 | Schlatter ................ A01N 25/02 504/100 |
| 7,056,862 | B2 | * | 6/2006 | Hayashi et al. ........... 504/116.1 |
| 2003/0158151 | A1 |   | 8/2003 | Wachendorff-Neumann et al. |
| 2005/0031653 | A1 | * | 2/2005 | Kwetkat et al. .............. 424/401 |
| 2005/0130913 | A1 |   | 6/2005 | Andersch et al. |
| 2005/0222051 | A1 |   | 10/2005 | Andersch et al. |

FOREIGN PATENT DOCUMENTS

| CN | 1698434 A | 11/2005 |
| EP | 0 422 803 A2 | 4/1991 |
| EP | 1023832 A1 * | 8/2000 | ............. A01N 25/04 |
| EP | 1623756 A1 * | 2/2006 | ............. A01N 25/04 |
| GB | 887303 | 1/1962 |
| GB | 1 425 810 | 2/1976 |
| JP | A-61-126001 | 6/1986 |
| JP | A-02-306902 | 12/1990 |
| JP | 03-173809 A | 7/1991 |
| JP | A-05-201801 | 8/1993 |
| JP | A 6-256122 | 9/1994 |
| JP | A-09-143003 | 6/1997 |
| JP | A-09-278602 | 10/1997 |
| JP | A-10-306001 | 11/1998 |
| JP | A-11-349418 | 12/1999 |
| JP | 2001-072508 A | 3/2001 |
| JP | 2001-072512 A | 3/2001 |
| JP | 2001-206808 A | 7/2001 |
| JP | 2002-012511 A | 1/2002 |
| JP | 2002-249403 A | 9/2002 |
| JP | A-2002-363005 | 12/2002 |
| JP | A-2003-073201 | 3/2003 |

(Continued)

OTHER PUBLICATIONS

Guide Chem, C2H4O2 [Downloaded Jul. 31, 2011] [Retrieved from internet <URL: http://www.guidechem.com/product/search_(C2H4O2)n.html >], 1 page.*
Merck Index Benzoic Acid (Knovel e-book, [downloaded Feb. 9, 2012]), 3 pages.*
Merck Index Salicylic Acid (Knovel e-book [Downloaded Feb. 9, 2012]), 3 pages.*
Tanaka et al. (JP 2001-206808; cited on IDS and Japanese Office Action; Machine Translation obtained from the JPO website and formatted on Feb. 8, 2012), 33 pages.*
University of Hearfordshire (Simeconazole, Pesticide Properties DataBase (last updated Jul. 25, 2013) [Retrieved from internet <URL: http://sitem.herts.ac.uk/aeru/ppdb/en/1204.htm >], 10 pages).*
JP 2002-012511 (Machine translation (English) from JPO website; [Downloaded Feb. 10, 2012], 12 pages).*

(Continued)

*Primary Examiner* — Ernst V Arnold
*Assistant Examiner* — Miriam A Levin
(74) *Attorney, Agent, or Firm* — Foley & Lardner LLP

(57) ABSTRACT

Provided is a pest control agent in the form of a suspension, which exhibits excellent dispersion stability for a long time without forming a hard cake due to settling and separation of solid particles or without losing fluidity due to gelation even when a cationic pest control active ingredient and/or an acid is used. Specifically provided is a pest control agent in the form of a suspension, which contains (a) a cationic pest control active ingredient and/or an acid, (b) a nonionic thickening agent, (c) a nonionic surface active agent, (d) a solid active ingredient and (e) water.

1 Claim, No Drawings

(56) References Cited

FOREIGN PATENT DOCUMENTS

| | | |
|---|---|---|
| JP | A-2004-143117 | 5/2004 |
| NZ | 322325 | 11/1999 |
| TW | 387791 B | 4/2000 |
| TW | 474907 B | 2/2002 |

OTHER PUBLICATIONS

University of Hertfordshire (Simeconazole, Pesticide Properties DataBase (last updated Jul. 25, 2013) [Retrieved from internet <URL: http://sitem.herts.ac.uk/aeru/ppdb/en/1204.htm >], 10 pages) (provided with prior office action).*
Khalil (Phase Separation of Cellulose Derivatives: Effects of Polymer Viscosity and Dielectric Constant of Nonsolvent, J. Pharmaceutical Sciences (1973) 62 (11): 1883, 1884), 2 pages.*
Phillips and Williams (Handbook of Hydrocolloids, Chap. 1, Introduction to food hydrocolloids (author = Williams), (Woodhead Pub. Ltd. and CRC Press LLC, 2000) front matter, table of contents (pp. vi-xii), Chap. 1 (pp. 1-19)), 29 pages.*
Dow, METHOCEL Cellulose Ethers, Technical Handbook (2002)(32 pages).*
Dow Wolff Cellulosics, Food & Nutrition, WALOCEL C, Sodium Carboxymethylcellulose, The ideal hydrocolloid for beverages [Downloaded from internet <URL:http://msdssearch.dow.com/PublishedLiteratureDOWCOM/dh_0152/0901b803801522b2.pdf?filepath=dowwolff/pdfs/nor >]; (date appears to be Aug. 2007 or Jul. 2008—see bottom of last page "0708") (36 pages).*
Reade (Reade SuperSite Search, Cordierite Powder [Retrieved from internet <URL: http://www.reade.com/products/29-minerals-and-ores-powder/148-magnesium-aluminosilicate-dichroite-iolite-cordierite-cordierite-powder-magnesium-alumia-silicate-alumino-magnesium-silicate-cas-1302-88-1 >], [Downloaded Jun. 23, 2015], 2 pages).*
Rowe et al. (Handbook of Pharmaceutical Excipients, Magnesium Aluminum Silicate (monograph), (Pharmaceutical Press 2009), title pages plus pp. 393-396; 8 pages total.*
Phillips et al., Handbook of Hydrocolloids, Chapter 1, Introduction to food hydrocolloids (Williams is first author of this chapter), (Woodhead Publishing, Ltd. 2000) title pages, TOC, pp. 1-19; 28 pages total.*
UC Davis, ChemWiki, 13.6: Aggregate particles in Aqueous Solution, [Retrieved from internet <URL: http://chemwiki.ucdavis.edu/Wikitexts/UC_Davis/UCD_Chem_2B/UCD_Chem_2B)%3A_Larsen/Unit_II%3A_States_of_Matter/Solutions/13.6%3A_Aggregate_Particles_in_Aqueous_Solution >], [Downloaded Jun. 18, 2015], 5 pages.*
McMahon (The Use of Non-Ionic Associative Polymers for the Thickening and Emulsifying of Personal Care Products (Part A) and the Synthesis of a Manganese Sod Mimetic for Reactive Coatings (Part B), Project Report in partial fulfillment of the requirements for a M.S. in Polymers and Coatings (Cal. Polytech. State Univ., Jun. 2011), 101 pages).*
Wamser (Organic Chemistry III, Chem 336, Spring 2000, Chapter 21—Amines, [Retrieved from internet <URL: http://web.pdx.edu/~wamserc/C336S00/21notes.htm .], 5 pages).*
Office Action issued in NZ 575290, dated Oct. 19, 2010.
Office Action issued in Taiwanese Patent Application No. 096133650, dated Nov. 5, 2010. (with English-language translation).
Office Action dated Sep. 27, 2011, in Korean Application No. 10-2009-7004849, with English translation, 6 pages.
Office Action dated Oct. 11, 2011, in Japanese Application No. 2008-534326, with English translation, 7 pages.
Office Action dated Oct. 11, 2011, in JP 2008-534326, with English translation, 7 pages.
Office Action dated Sep. 27, 2011, in KR 2009-7004849, with English translation, 6 pages.
Office Action dated Feb. 22, 2012, in CN 200780033364.8, with English translation, 10 pages.
Office Action dated Mar. 29, 2012, in TW 96133650, with English translation, 7 pages.
Office Action dated Oct. 13, 2013, in IL 197458, with English translation, 3 pages.

* cited by examiner

PEST CONTROL AGENT IN FORM OF STABLE SUSPENSION

This application is a National Stage (371) Application of PCT/JP2007/067584, filed in Japan on Sep. 10, 2007 (published as WO 2008/032671 A1 on Mar. 30 2008), which claims priority to a foreign application number JP-2006-246658, filed in Japan on Sep. 12, 2006, the entire disclosure of which is incorporated herein by reference.

TECHNICAL FIELD

The present invention relates to a pest control agent in the form of a suspension, which exhibits excellent dispersion stability for a long time without forming a hard cake due to settling and separation of solid particles or without losing fluidity due to gelation even when a cationic pest control active ingredient and/or an acid is used.

In addition, the present invention also relates to a pest control agent in the form of a suspension, which exhibits excellent dispersion stability for a long time without forming a hard cake due to settling and separation of solid particles or without losing fluidity due to gelation even when a cationic pest control active ingredient and/or an acid having an acid dissociation exponent (pKa) of 6 or less is used.

Priority is claimed on Japanese Patent Application No. 2006-246658, filed Sep. 12, 2006, the content of which is incorporated herein by reference.

BACKGROUND ART

Aqueous suspension formulations have been conventionally known as formulations containing a solid agricultural chemical active ingredient. Since water is the dispersion medium for these aqueous suspension formulations, they are less toxic, irritating, and have fewer problems of malodor and environmental pollution caused by organic solvents, and thus are advantageous as compared to other formulations using organic solvents.

The aqueous suspension formulations are prepared by grinding a solid agricultural chemical active ingredient into a powder having an average particle size of about 0.5 μm to 10 μm, mixing the powder with a surface active agent and, if necessary, a water soluble polymer or the like by using water as the dispersion medium, and stabilizing the mixture in the form of a suspension. The water soluble polymer used in this process is a thickening agent for adjusting the viscosity of the formulations, and anionic water soluble polymers (anionic thickening agent) are widely used.

However, if an anionic thickening agent is used concomitantly with a cationic compound (or an acid) when preparing the aqueous suspension formulations, the problems of the formation of a hard cake due to settling and separation of solid particles and the loss of fluidity due to gelation arise at times.

On the other hand, as the formulations using a nonionic thickening agent such as hydroxyalkyl cellulose, (i) an aqueous suspension formulation containing at least one active ingredient selected from an agricultural chemical active ingredient, an industrial antiseptic and antifungal active ingredient, and a household antiseptic and antifungal active ingredient, a water soluble cellulose ether, silica, and water (Patent Document 1); (ii) a granular agricultural chemical formulation containing an agricultural chemical active ingredient having a solubility of 100 ppm or more in water at 20° C., and hydroxypropyl methyl cellulose and/or methyl cellulose (Patent Document 2); a quick drying germicidal disinfectant formed by adding a hydrophobic hydroxypropyl methyl cellulose derivative, in which a long chain alkyl group is introduced, to a disinfectant composed of alcohols such as ethanol and a germicidal disinfectant (Patent Document 3); (iv) an aqueous suspension formulation formed of an insecticidal active ingredient or the like, a water soluble cellulose ether, and water (Patent Document 4); and the like have been known.

However, in these documents, there is no mention of suspension stability when a cationic pest control active ingredient is added to such compositions.

Patent Document 1: Japanese Unexamined Patent Application, First Publication No. 2004-143117
Patent Document 2: Japanese Unexamined Patent Application, First Publication No. 2003-073201
Patent Document 3: Japanese Unexamined Patent Application, First Publication No. Hei 11-349418
Patent Document 4: Japanese Unexamined Patent Application, First Publication No. Hei 10-306001

DISCLOSURE OF THE INVENTION

The present invention was completed in view of the above circumstances with regard to conventional techniques, and an object of the present invention is to provide a pest control agent in the form of a suspension, which exhibits excellent dispersion stability for a long time without forming a hard cake due to settling and separation of solid particles or without losing fluidity due to gelation even when a cationic pest control active ingredient and/or an acid is used.

As a result of intensive investigation aimed at achieving the above object, the present inventors discovered the following. With regard to the aqueous pest control agents in the form of a suspension which contain a solid active ingredient and a cationic pest control active ingredient and/or an acid, an aqueous pest control agent in the form of a suspension, which exhibits excellent dispersion stability for a long time without forming a hard cake due to settling and separation of solid active ingredients or without losing fluidity due to gelation can be achieved by using a combination of a cationic pest control active ingredient and/or an acid, a nonionic thickening agent, and a nonionic surface active agent. This discovery resulted in the present invention.

Thus, according to several aspects of the present invention, there are provided the following pest control agents in the form of a suspension, a production method thereof, and a method for stabilizing the pest control agents in the form of a suspension (1) to (11).

(1) A pest control agent in the form of a suspension containing: (a) a cationic pest control active ingredient and/or an acid; (b) a nonionic thickening agent; (c) a nonionic surface active agent; (d) a solid active ingredient; and (e) water.

(2) A pest control agent in the form of a suspension containing: (a) a cationic pest control active ingredient and/or an acid having an acid dissociation exponent (pKa) of 6 or less; (b) a nonionic thickening agent; (c) a nonionic surface active agent; (d) a solid active ingredient; and (e) water.

(3) The pest control agent in the form of a suspension according to the above (1) or (2) in which the cationic pest control active ingredient described in the above (1) or (2) is at least one selected from the group consisting of an iminoctadine salt, iminoctadine albesilate, iminoctadine acetate, emamectin benzoate, oxine sulfate, oxpoconazole fumarate, cartap, chlormequat, choline, diquat, streptomycin, propamocarb hydrochloride, mepiquat chloride, monofluoroacetate, levamisole hydrochloride, paraquat, and morantel tartrate.

(4) The pest control agent in the form of a suspension according to any one of the above (1) to (3) in which the acid described in the above (1) or the acid having an acid dissociation exponent (pKa) of 6 or less described in the above (2) is at least one selected from the group consisting of hydrobromic acid, hydrochloric acid, hydrofluoric acid, phosphoric acid, pyrophosphoric acid, tripolyphosphoric acid, sulfurous acid, sulfuric acid, glycolic acid, acetic acid, trimethylacetic acid, fluoroacetic acid, methoxyacetic acid, lactic acid, pyruvic acid, hexanoic acid, heptanoic acid, propionic acid, butyric acid, adipic acid, azelaic acid, oxaloacetic acid, citric acid, glutaric acid, succinic acid, oxalic acid, tartaric acid, suberic acid, fumaric acid, maleic acid, malonic acid, ascorbic acid, anisic acid, benzoic acid, cinnamic acid, phenylacetic acid, phenoxyacetic acid, phthalic acid, isophthalic acid, terephthalic acid, dodecylbenzene sulfonic acid, picric acid, and picolinic acid.

(5) The pest control agent in the form of a suspension according to any one of the above (1) to (4) in which the nonionic thickening agent described in the above (1) or (2) is at least one selected from the group consisting of a starch derivative, a plant extract derivative, and a cellulose derivative.

(6) The pest control agent in the form of a suspension according to any one of the above (1) to (5) in which the nonionic surface active agent described in the above (1) or (2) is at least one selected from the group consisting of a polyoxyalkylene alkyl ether, a polyoxyalkylene styryl phenyl ether, a polyoxyalkylene alkyl ester, a polyoxyalkylene sorbitan fatty acid ester, a polyoxyalkylene castor oil ether, a polyoxyethylene polyoxypropylene block polymer, and a polyoxyalkylene alkylamine.

(7) The pest control agent in the form of a suspension according to any one of the above (1) to (6) in which the solid active ingredient described in the above (1) or (2) is a compound having a melting point of 40° C. or more and a solubility of 1% by weight or less in water at 25° C.

(8) The pest control agent in the form of a suspension according to any one of the above (1) to (7) in which the amount of the cationic pest control active ingredient described in the above (1) or (2) is 5% by weight or more, with respect to the pest control agent as a whole.

(9) A method for producing the pest control agent in the form of a suspension according to any one of the above (1) to (8).

(10) A method for stabilizing a pest control agent in the form of a suspension containing: (a) a cationic pest control active ingredient and/or an acid; (b) a nonionic thickening agent; (c) a nonionic surface active agent; (d) a solid active ingredient; and (e) water.

(11) A method for stabilizing a pest control agent in the form of a suspension, the method including: mixing (c) a nonionic surface active agent, (d) a solid active ingredient, and (e) water; grinding the resulting mixture; and further mixing (a) a cationic pest control active ingredient diluted with water, and/or an acid, and (b) a nonionic thickening agent, thereby obtaining the pest control agent.

According to the present invention, there is provided a pest control agent in the form of a suspension, which exhibits excellent dispersion stability for a long time without forming a hard cake due to settling and separation of solid particles or without losing fluidity due to gelation even when a cationic pest control active ingredient and/or an acid is used.

In addition, according to the present invention, it is possible to provide an agricultural chemical composition having the following excellent effects: the amount of drugs can be reduced by adding a cationic pest control active ingredient, which has not been conventionally possible to mix with an agricultural chemical composition containing a solid active ingredient; the occurrence of phytotoxicity is reduced; also effective for drug-resistant microbes occurred due to use of a single agent; and synergistic effects due to the use of a mixed agent can be achieved.

BEST MODE FOR CARRYING OUT THE INVENTION

The present invention will be described in detail below.

A pest control agent in the form of a suspension according to the present invention contains (a) a cationic pest control active ingredient and/or an acid; (b) a nonionic thickening agent; (c) a nonionic surface active agent; (d) a solid active ingredient; and (e) water.

Component (a)

A component (a) of the pest control agent in the form of a suspension according to the present invention is a cationic pest control active ingredient and/or an acid.

Alternatively, the component (a) of the pest control agent in the form of a suspension according to the present invention is a cationic pest control active ingredient and/or an acid having an acid dissociation exponent (pKa) of 6 or less.

The phrase "a cationic pest control active ingredient and/or an acid" means that the component (a) of the pest control agent in the form of a suspension according to the present invention may be composed of a cationic pest control active ingredient alone, an acid alone, or a cationic pest control active ingredient and an acid.

(i) Cationic Active Ingredient

The cationic active ingredient used in the present invention is a pest control active ingredient that dissociates into ions in water and the atom group thereof has a positive charge.

In addition, the cationic pest control active ingredient used in the present invention is a pest control active ingredient that dissociates into ions in water and the atom group thereof that exhibits biocidal activity has a positive charge.

Examples of the pest control active ingredient include an agricultural or horticultural fungicidal active ingredient, an agricultural or horticultural insecticidal active ingredient, an agricultural or horticultural miticidal active ingredient, an industrial or household antiseptic active ingredient, and an industrial or household antifungal active ingredient.

The cationic active ingredient is not particularly limited. Typical examples thereof include iminoctadine, an iminoctadine salt, iminoctadine albesilate, iminoctadine acetate, emamectin benzoate, oxine sulfate, oxpoconazole fumarate, cartap, chlormequat, choline, diquat, streptomycin, propamocarb hydrochloride, mepiquat chloride, monofluoroacetate, levamisole hydrochloride, paraquat, and morantel tartrate.

These cationic active ingredients can be used singularly or in combination of two or more types thereof.

The amount of the cationic pest control active ingredient of the present invention is not particularly limited. However, the amount thereof may be 5% by weight or more, with respect to the agent as a whole, preferably 5-50% by weight, more preferably 5-30% by weight, and still more preferably 5-20% by weight.

(ii) Acid

The acid in the present invention is a substance that releases hydrogen ions when being formed into an aqueous solution. The acid of the present invention includes an inorganic acid and an organic acid.

In the present invention, among various acids, an acid having an acid dissociation exponent (pKa) of 6 or less, preferably one having an acid dissociation exponent (pKa) of 1 to 6, and more preferably one having an acid dissociation exponent (pKa) of 2 to 5 may be used.

The acid dissociation exponent (pKa) is a value calculated by the following way where the acid is represented by the symbol "HA". When the acid represented by the symbol HA is dissolved in water, the acid dissociates and releases hydrogen ions making the solution acidic. A hydrogen ion, a conjugate base of the acid and the undissociated acid simultaneously exist therein as described by the following dissociation equilibrium equation of Formula 1. In Formula 1, $H^+$ represents the concentration of hydrogen ion, $A^-$ represents the concentration of conjugate base of the acid, and HA represents the concentration of undissociated acid. When it comes to equilibrium under given conditions, the concentration ratio at both sides of the equation will become constant. The acid dissociation exponent (pKa) can be calculating by substituting the value of Ka, which is calculated based on formula 2, to Formula 3.

$$HA \rightleftarrows H^+ + A^- \quad \text{(Formula 1)}$$

$$Ka = \frac{[H^+][A^-]}{[HA]} \quad \text{(Formula 2)}$$

$$pKa = -\log_{10} Ka \quad \text{(Formula 3)}$$

Specific examples of the acid of the present invention include an inorganic acid such as hydrobromic acid, hydrochloric acid, hydrofluoric acid, phosphoric acid, pyrophosphoric acid, tripolyphosphoric acid, sulfurous acid, and sulfuric acid;

a saturated aliphatic monocarboxylic acid such as valeric acid, isovaleric acid, isobutyric acid, octanoic acid, formic acid, glycolic acid, acetic acid, trimethylacetic acid, fluoroacetic acid, methoxyacetic acid, lactic acid, pyruvic acid, hexanoic acid, heptanoic acid, propionic acid, and butyric acid;

an unsaturated aliphatic monocarboxylic acid such as acrylic acid; crotonic acid, vinyl acetic acid, and methacrylic acid;

an aliphatic polycarboxylic acid such as adipic acid, azelaic acid, oxaloacetic acid, citric acid, glutaric acid, succinic acid, oxalic acid, d-tartaric acid, tartaric acid (meso), suberic acid, fumaric acid, maleic acid, and malonic acid; and an organic acid such as ascorbic acid, anisic acid, benzoic acid, cinnamic acid, phenylacetic acid, phenoxyacetic acid, phthalic acid, isophthalic acid, terephthalic acid, dodecylbenzene sulfonic acid, picric acid, and picolinic acid. However, the acid of the present invention is not limited to these examples.

The amount of the acid added in the present invention is not particularly limited. However, the amount thereof may be preferably 0.01-30% by weight, with respect to the pest control agent as a whole, more preferably 0.1-10% by weight, and particularly preferably 0.5-5% by weight.

In addition, when a cationic pest control active ingredient and an acid are combined to prepare the component (a), the amount of the component (a) may be preferably 0.01-50% by weight, with respect to the pest control agent as a whole, more preferably 0.1-40% by weight, and still more preferably 5-30% by weight.

Component (b)

The component (b) of the pest control agent in the form of a suspension according to the present invention is a nonionic thickening agent.

A nonionic thickening agent is a compound which does not dissociate into ions in water and which increases the liquid viscosity.

The nonionic thickening agent used in the present invention is not particularly limited as long as the nonionic thickening agent is a compound which does not dissociate into ions in water and which increases the liquid viscosity. However, the nonionic thickening agent may be preferably at least one selected from the group consisting of a starch derivative, a plant extract derivative, and a cellulose derivative.

Examples of the starch derivative include amylose, amylopectin, carboxymethyl starch, floridean starch, and methyl starch.

Examples of the plant extract derivative include arabinan, propylene glycol alginate, propylene glycol alginate ester, guar gum, glucomannan, tamarind seed gum, tragacanth gum, pustulan, decomposed xyloglucan, HM pectin, LM pectin, and locust bean gum.

Examples of the cellulose derivative include ethyl cellulose, ethylhydroxyethyl cellulose, hydroxyethyl cellulose, hydroxypropyl cellulose, hydroxypropyl methyl cellulose, hydroxymethyl cellulose, methyl cellulose, and hydroxyethyl methyl cellulose.

These nonionic thickening agents can be used singularly or in combination of two or more types thereof.

Among these nonionic thickening agents, the use of a cellulose derivative, pullulan, pectin, propylene glycol alginate, and guar gum as the nonionic thickening agent of the present invention can achieve a pest control agent with satisfactory fluidity. Moreover, the nonionic thickening agent of the present invention may preferably be a cellulose derivative since the use thereof can achieve a pest control agent having even more excellent dispersion stability. Furthermore, the nonionic thickening agent of the present invention may more preferably be methyl cellulose, hydroxyethyl methyl cellulose, hydroxypropyl cellulose, and hydroxypropyl methyl cellulose, and may particularly preferably be hydroxypropyl methyl cellulose.

The amount of the nonionic thickening agent added in the present invention is not particularly limited. However, the mount thereof may preferably be 0.01-10% by weight, with respect to the pest control agent as a whole, more preferably 0.1-5% by weight, still more preferably 0.1-3% by weight, and particularly preferably 0.3-1% by weight.

Component (c)

The component (c) contained in the pest control agent in the form of a suspension according to the present invention is a nonionic surface active agent.

A nonionic surface active agent is a substance which does not dissociate into ions in water but exhibits an effect as a surfactant due to the balance between the hydrophobic group and the hydrophilic group within the agent.

The nonionic surface active agent used in the present invention is not particularly limited as long as it is a substance which does not dissociate into ions in water but exhibits an effect as a surfactant due to the balance between the hydrophobic group and the hydrophilic group within the agent. Examples of the nonionic surface active agent include a polyoxyalkylene nonionic surface active agent such as a polyoxyalkylene alkyl ether, a polyoxyalkylene arylphenyl ether, a polyoxyalkylene alkyl ester, a polyoxyalkylene sorbitan fatty acid ester, a polyoxyalkylene castor oil ether, a polyoxyethylene polyoxypropylene block polymer, and a polyoxyalkylene alkylamine.

Among these, the nonionic surface active agent used in the present invention may preferably be a polyoxyalkylene styryl phenyl ether. Among polyoxyalkylene styryl phenyl ethers, polyoxyethylene tristyryl phenyl ether, polyoxyethylene polyoxypropylene block polymer tristyryl phenyl ether, polyoxyethylene distyryl phenyl ether, polyoxyethylene polyoxypropylene block polymer distyryl phenyl ether, polyoxyethylene styryl phenyl ether, and polyoxyethylene polyoxypropylene block polymer styryl phenyl ether are more preferable, and polyoxyethylene tristyryl phenyl ether is particularly preferable.

These nonionic surface active agents can be used singularly or in combination of two or more types thereof.

The amount of the aforementioned nonionic surface active agent added in the present invention is not particularly limited. However, the amount thereof is preferably 0.01-50% by weight, with respect to the pest control agent as a whole, more preferably 0.1-10% by weight, still more preferably 0.5-5% by weight, and particularly preferably 0.5-2% by weight.

Component (d)

The component (d) of the pest control agent in the form of a suspension according to the present invention is a solid active ingredient.

The solid active ingredient used in the present invention is a solid active ingredient having pest control activity. In addition, the solid active ingredient used in the present invention is not particularly limited as long as it is a substance in a solid state at normal temperature (20 to 25° C.). However, it is preferable that the solid active ingredient has a melting point of 40° C. or more and a solubility of 1% by weight or less in water at 25° C.

Examples of the solid active ingredient include an agricultural or horticultural fungicidal active ingredient, an agricultural or horticultural insecticidal active ingredient, an agricultural or horticultural miticidal active ingredient, an industrial or household antiseptic active ingredient, and an industrial or household antifungal active ingredient.

As examples of such solid active ingredients, the following fungicides, insecticides, miticides, plant growth regulators, herbicides, rodenticides, bactericides, antifungal agents, and algicides may be exemplified. These solid active ingredients can be used singularly or in combination of two or more types thereof.

Examples of the fungicides include diclocymet, famoxadone, cyazofamid, thifluzamide, fluazinam, kresoxim-methyl, oxolinic acid, carpropamid, fenbuconazole, azoxystrobin, cyprodinil, dimethomorph, fenhexamid, diflumetorim, simeconazole, pyrimethanil, metominostrobin, bitertanol, thiabendazole, ziram, oxine-copper, dichlone, pencycuron, dithianon, cyflufenamid, PCNB, diclomezine, TPN, chinomethionat, tolclofos-methyl, difolatan, imibenconazole, propineb, oxycarboxin, cymoxanil, mepronil, dimethirimol, iprodione, fenarimol, tecloftalam, myclobutanil, difenoconazole, maneb, tricyclazole, ferimzone, hexaconazole, thiuram (TMTD), fthalide, flusulfamide, manzeb, diethofencarb, thiophanate-methyl, captan, vinclozolin, prochloraz, oxadixyl, benomyl, pyrazophos, procymidone, pyroquilon, isoprothiolane, CNA, ipconazole, triadimefon, anirazine, chloroneb, carbendazol, metalaxyl, triforine, flutolanil, oxpoconazole-fumarate, binapacryl, dazomet, PCP, tebuconazole, copper sulfate, carbendazin, dichlorophen, dichlone, tecloftalam and bethoxazin.

Examples of the insecticides include acequinocyl, etoxazole, tolfenpyrad, chlorfenapyr, pyriproxyfen, chromafenozide, fipronil, methoxyfenozide, milbemectin, furathiocarb, emamectin benzoate, thiacloprid, bifenazate, cadusafos, acetamiprid, lufenuron, phenisobromolate, tebufenozide, nemadectin, cyhalothrin, fenpropathrin, chlorfluazuron, tefluthrin, teflubenzuron, resmethrin, cycloprothrin, diflubenzuron, bifenthrin, cypermethrin, benzoepin, fluacrypyrim, bensultap, chlorpyrifos, phosalone, CVMP, NAC, dimethylvinphos, PHC, cyfluthrin, mesulfenfos, PMP, MTMC, MIPC, bendiocarb, pirimicarb, clothianidin, thiodicarb, chlorpyrifos-methyl, thiamethoxam, XMC, salithion, imidacloprid, MPMC, fenoxycarb, BHC, tralomethrin, pyridaphenthion, pirimiphos-methyl, pirimiphos-methyl, amitraz, buprofezin, DCIP, and bifenthrin.

Examples of the miticides include dienochlor, clofentezine, flufenoxuron, fenbutatin oxide, fenpyroximate, tetradifon, hexythiazox, kelthane, tebufenpyrad, alanycarb, benzomate, and fenothiocarb.

Examples of the plant growth regulators include inabenfide, flurprimidol, mefluidide, ethychlozate, paclobutrazol, forchlorfenuron, maleic hydrazide, gibberellin, ancymidol, and uniconazole.

Examples of the herbicides include clomeprop, pyraflufen ethyl, benzobicyclon, oxaziclomefone, pentoxazone, pyributicarb, pyrazoxyfen, etobenzanid, cumyluron, flumioxazin, chlorphthalim, anilofos, indanofan, amiprophos methyl, ethoxysulfuron, imazaquin, tepraloxydim, an MDBA isopropylamine salt, MCPA, imazamox-ammonium, prodiamine, pyrazolate, benzofenap, trifluralin, CNP, chlormetoxinyl, pendimethalin, quizalofop-ethyl, bifenox, oxadiargyl, TCTP, bethrodine, fenoxaprop-ethyl, oxadiazon, dithiopyr, isoxaben, daimuron, metribuzin, thenylchlor, methyl-dymron, DCPA, pyrazosulfuron ethyl, propyzamide, flazasulfuron, cyanazin, DBN, siduron, ametryn, bensulfuron-methyl, thiazafluoron, alachlor, tebuthiuron, diphenamid, metsulfuron-methyl, bromobutide, atrazine, ethidimuron, imazosulfuron, karbutilate, prometryn, PAC, dichlorprop, mephenacet, phenmedipham, asulam, triclopyr, DCMU, picloram, MCPB, simetryn, propazine-based dimethametryn, ioxynil, bentazone, desmetryne, lenacil, CAT, triaziflam, MDBA, thifensulfuron-methyl, terbacil, napropamide, MCP, MCPP, isouron, linuron, bromacil, fluthiacetmethyl, IPC, DCBN, imazapyr, endothal, quinoclamine, quinonamid, simazine, fentin, and DCMU.

Examples of the rodenticides include diphacinone, and coumarin-based rodenticides such as coumatetralyl.

Examples of the bactericides include oxolinic acid, nitrapyrin, oxytetracycline, 4-chloro-3,5-dimethylphenol, n-butyl-1,2-benzisothiazolin-3-one, 4,5-dichloro-2-n-octyl-4-isothiazolin-3-one, bis(2-pyridylthio-1-oxide), and 1,2-benzisothiazolin-3-one.

Examples of the antifungal agents include 2,3,5,6-tetrachloro-4-(methylsulfonyl)pyridine, and 3-iodo-2-propynyl butylcarbamate.

Examples of the algicides include cybutryne.

The amount of the solid active ingredient added in the present invention is not particularly limited. However, is the amount thereof may preferably be 0.01-70% by weight, with respect to the pest control agent as a whole, more preferably 0.1-60% by weight, still more preferably 5-50% by weight, and particularly preferably 10-40% by weight.

The pest control agent in the form of a suspension according to the present invention is a formulation which exhibits excellent dispersion stability for a long time without forming a hard cake due to settling and separation of solid particles or without losing fluidity due to gelation even when a solid active ingredient is contained in high concentration.
Component (e)

The component (e) of the pest control agent in the form of a suspension according to the present invention is water.

The water used in the present invention is not particularly limited. However, water with few impurities is preferable. For example, tap water, well water, distilled water, deionized water, or the like may be used.

In addition, the water may be soft water or hard water. Examples of hard water include CIPAC standard water D (342 ppm $Ca^{2+}:Mg^{2+}=4:1$) in accordance with the CIPAC (Collaborative International Pesticide Analytical Council) method.

The amount of water added in the present invention is not particularly limited. However, the amount thereof may preferably be 1-95% by weight, with respect to the pest control agent as a whole, more preferably 10-80% by weight, and particularly preferably 30-70% by weight.

Besides the abovementioned components (a) to (e), the pest control agent in the form of a suspension according to the present invention may further contain an optional component such as an antifreezing agent, an antifoaming agent, or a preservative.

Examples of the antifreezing agent to be used include glycols such as ethylene glycol, ethyl diglycol, ethyl triglycol, propylene glycol, dipropylene glycol, tripropylene glycol, diethylene glycol, butanediol, and butyl diglycol.

Examples of the antifoaming agent include silicone-based antifoaming agents such as polydimethylsiloxane (for example, Antifoam SE39 manufactured by Wacker Asahikasei Silicone Co., Ltd.).

Examples of the preservative include 1,2-benzisothiazolin-3-one, 5-chloro-2-methyl-4-isothiazolin-3-one, 2-methyl-4-isothiazolin-3-one, ascorbic acid, hexamethylenetetramine, sodium propionate, sorbic acid, a sulfurous acid solution, paraformaldehyde, benzoic acid, propyl p-hydroxybenzoate, methyl p-hydroxybenzoate, sodium benzoate, ascorbic acid, ascorbyl palmitate, and sodium 1,1'-biphenyl-2-olate. Examples of commercially available formulation products containing these preservatives include Denicide BIT-20N (manufactured by Nagase ChemteX Corporation), Legend MK (manufactured by Rohm and Haas Company), and Proxel GXL (manufactured by Avecia Biologics Ltd.).
(Preparation of Formulations)

The pest control agent in the form of a suspension according to the present invention can be prepared by, for example, mixing the aforementioned components (c), (d), and (e) together with other optional components in a predetermined ratio and wet grinding the mixture using a well-known wet grinding machine, thereby obtaining a wet milled product, and then adding predetermined amounts of the aforementioned components (a) and (b) to the obtained wet milled product and stirring the resulting mixture.

The pest control agent in the form of a suspension according to the present invention obtained in the manner described above has excellent fluidity. That is, the pest control agent in the form of a suspension according to the present invention can be said to have excellent fluidity due to the following reason: when the pest control agent in the form of a suspension according to the present invention is poured into an upright glass test tube (having a flat bottom cylindrical shape with an inner diameter of 30 mm and a height of 120 mm) until the poured agent reaches 55 mm from the bottom of the test tube and then the test tube is placed horizontally, it takes only 90 seconds or less for the agent to reach the point 85 mm from the bottom of the test tube. This is the same as the definition of the term "liquid state" provided in Article 69-2 of the "Regulations on Hazardous Material Control" in Japan.

EXAMPLES

The present invention will be described in even more detail using Examples and Comparative Examples below. However, the scope of the present invention is not limited to the following Examples. The term "parts" refers to "parts by weight" in the Examples and the Comparative Examples.

Example 1

2 parts of polyoxyethylene (14 mol) tristyryl phenyl ether (manufactured by Takemoto Oil & Fat Co., Ltd.) was heated, and 0.1 parts of 1,2-benzisothiazolin-3-one (Denicide BIT-20N manufactured by Nagase ChemteX Corporation) was then added thereto, and the resulting mixture was then dissolved in 2 parts of propylene glycol (antifreezing agent). To the obtained solution, 27.5 parts of water, 0.5 parts of a silicone-based antifoaming agent (Antifoam SE39 manufactured by Wacker Asahikasei Silicone Co., Ltd.), and 27.4 parts of thiophanate-methyl were added and mixed. A wet milling process was carried out using a Dyno Mill (KDL type manufactured by Shinmaru Enterprises Corporation) by filling the device with 510 ml of glass beads (high beads D-16 having a size of 1.1-1.5 mm) (filling rate: 85%) under the conditions of a rotational frequency (peripheral speed) of 3,000 rpm (60 mm in diameter, 15 msec) and a supply rate of 51 g/min, thereby obtaining a wet milled product. By mixing the wet milled product with a solution, which was formed by dissolving 0.5 parts of methyl cellulose (Metolose SM-400 manufactured by Shin-Etsu Chemical Co., Ltd., where the numeral on the right hand side of the product name "Metolose" represents the viscosity (mPa·s) in an aqueous solution of 2% by weight) in 40 parts of a 40% aqueous iminoctadine acetate solution in advance, a pest control agent in the form of a suspension (hereafter referred to as "suspension composition") 1 was obtained.

Example 2

By carrying out the same operation as that in Example 1 except using methyl cellulose (Metolose SM-1500 manufactured by Shin-Etsu Chemical Co., Ltd., where the numeral on the right hand side of the product name "Metolose" represents the viscosity (mPa·s) in an aqueous solution of 2% by weight) instead of methyl cellulose (Metolose SM-400 manufactured by Shin-Etsu Chemical Co., Ltd.), a suspension composition 2 was obtained.

Example 3

By carrying out the same operation as that in Example 1 except using methyl cellulose (Metolose SM-4000 manufactured by Shin-Etsu Chemical Co., Ltd., where the numeral on the right hand side of the product name "Metolose" represents the viscosity (mPa·s) in an aqueous solution of 2% by weight) instead of methyl cellulose (Metolose SM-400 manufactured by Shin-Etsu Chemical Co., Ltd.), a suspension composition 3 was obtained.

Example 4

By carrying out the same operation as that in Example 1 except using hydroxypropyl methyl cellulose (Metolose 60SH-4000 manufactured by Shin-Etsu Chemical Co., Ltd., where the numeral on the right hand side of the product name "Metolose" represents the viscosity (mPa·s) in an aqueous solution of 2% by weight) instead of methyl cellulose (Metolose SM-400 manufactured by Shin-Etsu Chemical Co., Ltd.), a suspension composition 4 was obtained.

Example 5

By carrying out the same operation as that in Example 1 except using hydroxypropyl methyl cellulose (Metolose 65SH-1500 manufactured by Shin-Etsu Chemical Co., Ltd., where the numeral on the right hand side of the product name "Metolose" represents the viscosity (mPa·s) in an aqueous solution of 2% by weight) instead of methyl cellulose (Metolose SM-400 manufactured by Shin-Etsu Chemical Co., Ltd.), a suspension composition 5 was obtained.

Example 6

By carrying out the same operation as that in Example 1 except using hydroxypropyl methyl cellulose (Metolose 65SH-4000 manufactured by Shin-Etsu Chemical Co., Ltd., where the numeral on the right hand side of the product name "Metolose" represents the viscosity (mPa·s) in an aqueous solution of 2% by weight) instead of methyl cellulose (Metolose SM-400 manufactured by Shin-Etsu Chemical Co., Ltd.), a suspension composition 6 was obtained.

Example 7

By carrying out the same operation as that in Example 1 except using hydroxypropyl methyl cellulose (Metolose 90SH-400 manufactured by Shin-Etsu Chemical Co., Ltd., where the numeral on the right hand side of the product name "Metolose" represents the viscosity (mPa·s) in an aqueous solution of 2% by weight) instead of methyl cellulose (Metolose SM-400 manufactured by Shin-Etsu Chemical Co., Ltd.), a suspension composition 7 was obtained.

Example 8

By carrying out the same operation as that in Example 1 except using hydroxypropyl methyl cellulose (Metolose 90SH-4000 manufactured by Shin-Etsu Chemical Co., Ltd., where the numeral on the right hand side of the product name "Metolose" represents the viscosity (mPa·s) in an aqueous solution of 2% by weight) instead of methyl cellulose (Metolose SM-400 manufactured by Shin-Etsu Chemical Co., Ltd.), a suspension composition 8 was obtained.

Example 9

By carrying out the same operation as that in Example 1 except using methyl cellulose (manufactured by Wako Pure Chemical Industries, Ltd. and having a viscosity of 400 mPa·s in an aqueous solution of 2% by weight at 20° C.) instead of methyl cellulose (Metolose SM-400 manufactured by Shin-Etsu Chemical Co., Ltd.), a suspension composition 9 was obtained.

Example 10

By carrying out the same operation as that in Example 1 except using hydroxypropyl cellulose (HPC-M manufactured by Nippon Soda Co., Ltd. and having a viscosity of 150-400 mPa·s in an aqueous solution of 2% by weight at 20° C.) instead of methyl cellulose (Metolose SM-400 manufactured by Shin-Etsu Chemical Co., Ltd.), a suspension composition 10 was obtained.

Example 11

By carrying out the same operation as that in Example 1 except using hydroxypropyl cellulose (HPC-H manufactured by Nippon Soda Co., Ltd. and having a viscosity of 1,000-4,000 mPa·s in an aqueous solution of 2% by weight at 20° C.) instead of methyl cellulose (Metolose SM-400 manufactured by Shin-Etsu Chemical Co., Ltd.), a suspension composition 11 was obtained.

Example 12

By carrying out the same operation as that in Example 1 except using pullulan (manufactured by Hayashibara Shoji, Inc. and having a viscosity of 50 mPa·s in an aqueous solution of 2% by weight) instead of methyl cellulose (Metolose SM-400 manufactured by Shin-Etsu Chemical Co., Ltd.), a suspension composition 12 was obtained.

Example 13

By carrying out the same operation as that in Example 1 except using Pectin LM-5CS (manufactured by CP Kelco and having a degree of esterification of 5) instead of methyl cellulose (Metolose SM-400 manufactured by Shin-Etsu Chemical Co., Ltd.), a suspension composition 13 was obtained.

Example 14

By carrying out the same operation as that in Example 1 except using Pectin FREEZE-J (manufactured by CP Kelco and having a degree of esterification of 72) instead of methyl cellulose (Metolose SM-400 manufactured by Shin-Etsu Chemical Co., Ltd.), a suspension composition 14 was obtained.

Example 15

By carrying out the same operation as that in Example 1 except using Pectin YM-150-LJ (manufactured by CP Kelco and having a degree of esterification of 72) instead of methyl cellulose (Metolose SM-400 manufactured by Shin-Etsu Chemical Co., Ltd.), a suspension composition 15 was obtained.

Example 16

By carrying out the same operation as that in Example 1 except using Kimiloid MV (propylene glycol alginate manufactured by Kimica Corporation and having a viscosity of 100-150 mPa·s in an aqueous solution of 1% by weight at 20° C.) instead of methyl cellulose (Metolose SM-400 manufactured by Shin-Etsu Chemical Co., Ltd.), a suspension composition 16 was obtained.

Example 17

By carrying out the same operation as that in Example 1 except using guar gum (manufactured by CP Kelco and having a viscosity of 3,000-6,000 mPa·s in an aqueous solution of 1% by weight instead of methyl cellulose (Metolose SM-400 manufactured by Shin-Etsu Chemical Co., Ltd.), a suspension composition 17 was obtained.

Example 18

By carrying out the same operation as that in Example 1 except using Kimiloid HV (propylene glycol alginate manufactured by Kimica Corporation and having a viscosity of 150-250 mPa·s in an aqueous solution of 1% by weight at 20° C.) instead of methyl cellulose (Metolose SM-400 manufactured by Shin-Etsu Chemical Co., Ltd.), a suspension composition 18 was obtained.

Example 19

2 parts of polyoxyethylene (14 mol) tristyryl phenyl ether (manufactured by Takemoto Oil & Fat Co., Ltd.) was heated, and 0.1 parts of 1,2-benzisothiazolin-3-one (Denicide BIT-20N manufactured by Nagase ChemteX Corporation) was then added thereto, and the resulting mixture was then dissolved in 2 parts of propylene glycol (antifreezing agent). To the obtained solution, 24.9 parts of water, 0.5 parts of a silicone-based antifoaming agent (Antifoam SE39 manufactured by Wacker Asahikasei Silicone Co., Ltd.), and 50 parts of thiophanate-methyl were added and mixed. A wet milling process was carried out using a Dyno Mill (KDL type manufactured by Shinmaru Enterprises Corporation) by filling the device with 510 ml of glass beads (high beads D-16 having a size of 1.1-1.5 mm) (filling rate: 85%) under the conditions of a rotational frequency (peripheral speed) of 3,000 rpm (60 mm in diameter, 15 m/sec) and a supply rate of 51 g/min, thereby obtaining a wet milled product.

By mixing the wet milled product with a solution, which was formed by dissolving 0.5 parts of hydroxypropyl methyl cellulose (Metolose 90SH-400 manufactured by Shin-Etsu Chemical Co., Ltd., where the numeral on the right hand side of the product name "Metolose" represents the viscosity (mPa·s) in an aqueous solution of 2% by weight) in 20 parts of a 40% aqueous iminoctadine acetate solution in advance, a suspension composition 19 was obtained.

Example 20

2 parts of polyoxyethylene (14 mol) tristyryl phenyl ether (manufactured by Takemoto Oil & Fat Co., Ltd.) were heated, and 0.1 parts of Denicide BIT-20N were then added thereto, and the resulting mixture was then dissolved in 2 parts of propylene glycol. To the obtained solution, 20.95 parts of water and 0.5 parts of Antifoam SE39 were added and mixed, and then 27.3 parts of thiophanate-methyl were added to the mixture and mixed. A wet milling process was carried out using a Dyno Mill (KDL type) by filling the device with 510 ml of glass beads (high beads D-16 having a size of 1.1-1.5 mm) (filling rate: 85%) under the conditions of a rotational frequency (peripheral speed) of 3,000 rpm (60 mm in diameter, 15 msec) and a supply rate of 51 g/min, thereby obtaining a wet milled product.

By mixing the wet milled product with a solution, which was formed by dissolving 0.14 parts of an antimicrobial agent (Legend MK manufactured by Rohm and Haas Company) containing 1.05-1.25% of methylchloroisothiazoline and 0.25-0.45% of methylisothiazoline, and 1.5 parts of hydroxypropyl methyl cellulose (Metolose 90SH-400 manufactured by Shin-Etsu Chemical Co., Ltd., where the numeral on the right hand side of the product name "Metolose" represents the viscosity (mPa·s) in an aqueous solution of 2% by weight) in 42.51 parts of water in advance, and then further mixing 3 parts of citric acid (manufactured by Nacalai Tesque, Inc.) with the resulting mixture, a suspension composition 20 was obtained.

Example 21

By carrying out the same operation as that in Example 20 except using 3 parts of phosphoric acid (manufactured by Nacalai Tesque, Inc.) instead of 3 parts of citric acid, a suspension composition 21 was obtained.

Example 22

By carrying out the same operation as that in Example 20 except changing the amount of water from 42.51 parts to 40.41 parts and using 3.6 parts of methyl cellulose (Metolose SM-15 manufactured by Shin-Etsu Chemical Co., Ltd., where the numeral on the right hand side of the product name "Metolose" represents the viscosity (mPa·s) in an aqueous solution of 2% by weight) instead of 1.5 parts of hydroxypropyl methyl cellulose (Metolose 90SH-400 manufactured by Shin-Etsu Chemical Co., Ltd.), a suspension composition 22 was obtained.

Example 23

By carrying out the same operation as that in Example 22 except using 3 parts of phosphoric acid instead of 3 parts of citric acid, a suspension composition 23 was obtained.

Example 24

2 parts of polyoxyethylene arylphenyl ether (manufactured by Takemoto Oil & Fat Co., Ltd.) was heated, and 0.1 parts of 1,2-benzisothiazolin-3-one (Denicide BIT-20N manufactured by Nagase ChemteX Corporation) was then added thereto, and the resulting mixture was then dissolved in 2 parts of propylene glycol (antifreezing agent). To the obtained solution, 26.26 parts of water, 0.25 parts of a silicone-based antifoaming agent (Antifoam SE39 manufactured by Wacker Asahikasei Silicone Co., Ltd.), and 27.3 parts of thiophanate-methyl were added and mixed. A wet milling process was carried out using a Dyno Mill (KDL type manufactured by Shinmaru Enterprises Corporation) by filling the device with 510 ml of glass beads (high beads D-16 having a size of 1.1-1.5 mm) (filling rate: 85%) under the conditions of a rotational frequency (peripheral speed) of 3,000 rpm (60 mm in diameter, 15 msec) and a supply rate of 51 g/min, thereby obtaining a wet milled product. By mixing the wet milled product with a solution, which was formed by dissolving 0.14 parts of an antimicrobial agent (Legend MK manufactured by Rohm and Haas Company) containing 1.05-1.25% of methylchloroisothiazoline and 0.25-0.45% of methylisothiazoline, 0.25 parts of a silicone-based antifoaming agent (Antifoam SE39 manufactured by Wacker Asahikasei Silicone Co., Ltd.), and 0.7 parts of hydroxypropyl methyl cellulose (Metolose 90SH-400 manufactured by Shin-Etsu Chemical Co., Ltd., where the numeral on the right hand side of the product name "Metolose" represents the viscosity (mPa·s) in an aqueous solution of 2% by weight) in 40 parts of a 40% aqueous iminoctadine acetate solution in advance, and then further adding and mixing 1 part of acetic acid (manufactured by Nippon Synthetic Chemical Industry Co., Ltd.) with the resulting mixture, a suspension composition 24 was obtained.

Comparative Example 1

By carrying out the same operation as that in Example 1 except using an inorganic thickening agent (Kunipia F which was sodium bentonite manufactured by Kunimine Industries Co., Ltd.) instead of methyl cellulose (Metolose SM-400 manufactured by Shin-Etsu Chemical Co., Ltd.), a suspension composition 25 was obtained.

Comparative Example 2

By carrying out the same operation as that in Example 1 except using iota carrageenan (GENU VISCO J-J manufactured by CP Kelco) instead of methyl cellulose (Metolose SM-400 manufactured by Shin-Etsu Chemical Co., Ltd.), a suspension composition 26 was obtained.

Comparative Example 3

By carrying out the same operation as that in Example 1 except using xanthan gum (Rhodopol 23 manufactured by Rhone-Poulenc) instead of methyl cellulose (Metolose SM-400 manufactured by Shin-Etsu Chemical Co., Ltd.), a suspension composition 27 was obtained.

Comparative Example 4

By carrying out the same operation as that in Example 1 except using kappa carrageenan (GENU GEL WG-108 manufactured by CP Kelco) instead of methyl cellulose (Metolose SM-400 manufactured by Shin-Etsu Chemical Co., Ltd.), a suspension composition 28 was obtained.

Comparative Example 5

By carrying out the same operation as that in Example 19 except not using polyoxyethylene (14 mol) tristyryl phenyl ether (manufactured by Takemoto Oil & Fat Co., Ltd.), changing the amount of thiophanate-methyl from 50 parts to 27.4 parts, changing the amount of 40% aqueous iminoctadine acetate solution from 20 parts to 40 parts, and changing the amount of water from 24.9 parts to 29.5 parts, a suspension composition 29 was obtained.

Comparative Example 6

By carrying out the same operation as that in Example 19 except not using polyoxyethylene (14 mol) tristyryl phenyl ether (manufactured by Takemoto Oil & Fat Co., Ltd.) and a 40% aqueous iminoctadine acetate solution and changing the amount of water from 24.9 parts to 46.9 parts, a suspension composition 30 was obtained.

Comparative Example 7

By carrying out the same operation as that in Example 19 except not using polyoxyethylene (14 mol) tristyryl phenyl ether (manufactured by Takemoto Oil & Fat Co., Ltd.) and changing the amount of water from 24.9 parts to 26.9 parts, a suspension composition 31 was obtained.

Comparative Example 8

By carrying out the same operation as that in Example 20 except changing the amount of water from 42.51 parts to 43.71 parts and using 0.3 parts of xanthan gum (manufactured by CP Kelco) instead of 1.5 parts of hydroxypropyl methyl cellulose (Metolose 90SH-400 manufactured by Shin-Etsu Chemical Co., Ltd.), a suspension composition 32 was obtained.

Comparative Example 9

By carrying out the same operation as that in Example 20 except changing the amount of water from 42.51 parts to 43.71 parts, using 0.3 parts of xanthan gum (manufactured by CP Kelco) instead of 1.5 parts of hydroxypropyl methyl cellulose (Metolose 90SH-400 manufactured by Shin-Etsu Chemical Co., Ltd.), and using 3 parts of phosphoric acid instead of 3 parts of citric acid, a suspension composition 33 was obtained.

(Test Example 1) Fluidity Test

The suspension compositions 1 to 19 obtained in Examples 1 to 19 and the suspension compositions 25 to 31 obtained in Comparative Examples 1 to 7 were each poured into an upright glass test tube (having a flat bottom cylindrical shape with an inner diameter of 30 mm and a height of 120 mm, hereafter simply referred to as "test tube") until the poured composition reached 55 mm from the bottom of the test tube and then the test tube was placed horizontally. The time required for each of the compositions to reach the point 85 mm from the bottom of the test tube was measured. When the measured time was 90 seconds or less, the composition was evaluated to have fluidity. On the other hand, when the measured time was longer than 90 seconds, the composition was evaluated to have no fluidity. This is the same as the definition of the term "liquid state" provided in Article 69-2 of the "Regulations on Hazardous Material Control" in Japan. The evaluation results are shown in Table 1.

In Table 1, the composition with fluidity is indicated as "superior" whereas the composition with no fluidity is indicated as "inferior".

In Table 1, the components (a), (b), (c), (d), and (e) represent a cationic pest control active ingredient, a nonionic thickening agent, a nonionic surface active agent, a solid active ingredient, and water, respectively. The same also applies to the following Table 2.

TABLE 1

| | Suspension Composition | Component (a) (parts by weight) | Component (b) (parts by weight) | Component (c) (parts by weight) | Component (d) (parts by weight) | Component (e) (parts by weight) | Fluidity |
|---|---|---|---|---|---|---|---|
| Ex. 1 | 1 | 16 | 0.5 | 2 | 27.4 | 51.5 | Superior |
| Ex. 2 | 2 | 16 | 0.5 | 2 | 27.4 | 51.5 | Superior |

TABLE 1-continued

| | Suspension Composition | Component (a) (parts by weight) | Component (b) (parts by weight) | Component (c) (parts by weight) | Component (d) (parts by weight) | Component (e) (parts by weight) | Fluidity |
|---|---|---|---|---|---|---|---|
| Ex. 3 | 3 | 16 | 0.5 | 2 | 27.4 | 51.5 | Superior |
| Ex. 4 | 4 | 16 | 0.5 | 2 | 27.4 | 51.5 | Superior |
| Ex. 5 | 5 | 16 | 0.5 | 2 | 27.4 | 51.5 | Superior |
| Ex. 6 | 6 | 16 | 0.5 | 2 | 27.4 | 51.5 | Superior |
| Ex. 7 | 7 | 16 | 0.5 | 2 | 27.4 | 51.5 | Superior |
| Ex. 8 | 8 | 16 | 0.5 | 2 | 27.4 | 51.5 | Superior |
| Ex. 9 | 9 | 16 | 0.5 | 2 | 27.4 | 51.5 | Superior |
| Ex. 10 | 10 | 16 | 0.5 | 2 | 27.4 | 51.5 | Superior |
| Ex. 11 | 11 | 16 | 0.5 | 2 | 27.4 | 51.5 | Superior |
| Ex. 12 | 12 | 16 | 0.5 | 2 | 27.4 | 51.5 | Superior |
| Ex. 13 | 13 | 16 | 0.5 | 2 | 27.4 | 51.5 | Superior |
| Ex. 14 | 14 | 16 | 0.5 | 2 | 27.4 | 51.5 | Superior |
| Ex. 15 | 15 | 16 | 0.5 | 2 | 27.4 | 51.5 | Superior |
| Ex. 16 | 16 | 16 | 0.5 | 2 | 27.4 | 51.5 | Superior |
| Ex. 17 | 17 | 16 | 0.5 | 2 | 27.4 | 51.5 | Superior |
| Ex. 18 | 18 | 16 | 0.5 | 2 | 27.4 | 51.5 | Superior |
| Ex. 19 | 19 | 8 | 0.5 | 2 | 50 | 36.9 | Superior |
| Comp. Ex. 1 | 25 | 16 | — | 2 | 27.4 | 51.5 | Inferior |
| Comp. Ex. 2 | 26 | 16 | — | 2 | 27.4 | 51.5 | Inferior |
| Comp. Ex. 3 | 27 | 16 | — | 2 | 27.4 | 51.5 | Inferior |
| Comp. Ex. 4 | 28 | 16 | — | 2 | 27.4 | 51.5 | Inferior |
| Comp. Ex. 5 | 29 | 16 | 0.5 | — | 27.4 | 53.5 | Inferior |
| Comp. Ex. 6 | 30 | — | 0.5 | — | 50 | 46.9 | Inferior |
| Comp. Ex. 7 | 31 | 8 | 0.5 | — | 50 | 38.9 | Inferior |

From the results shown in Table 1, it was apparent that the suspension compositions of Examples 1 to 19 had excellent fluidity.

On the other hand, the suspension compositions of Comparative Examples 1 to 4 with no added component (b) and the suspension compositions of Comparative Examples 5 to 7 with no added component (c) had inferior fluidity.

(Test Example 2) Measurement of Supernatant Separation Rate

The suspension compositions 20 to 23 obtained in Examples 20 to 23 and the suspension compositions 32 and 33 obtained in Comparative Examples 8 and 9 were each poured into an upright test tube until the poured composition reached about 70 mm from the bottom of the test tube. The test tubes were left to stand for 1 month in a temperature-controlled bath in which the temperature was controlled to repeat a temperature cycle of −10° C. for 3 days and 50° C. for 3 days. The supernatant separation rate was calculated by dividing the height of the supernatant fraction by the height of the overall sample. A sample with a low supernatant separation rate, that is, that with a supernatant separation rate of 20% or less, is preferable, 10% or less is more preferable, and 5% or less is particularly preferable. The results are shown in Table 2. In Table 2, the components (a), (b), (c), (d), and (e) represent an acid, a nonionic thickening agent, a nonionic surface active agent, a solid active ingredient, and water, respectively.

From the results shown in Table 2, it was apparent that the suspension compositions of Examples 20 to 23 had low supernatant separation rates, as compared to those of the suspension compositions of Comparative Examples 8 and 9, and thus had excellent dispersion stability.

When the fluidity test (Test Example 1) and the measurement of the supernatant separation rate (Test Example 2) were conducted in the same manner using the suspension composition 24 of Example 24, the results showed that the suspension composition 24 had fluidity and its supernatant separation rate, which was 3%, was also low.

The invention claimed is:

1. A pest control agent in the form of a suspension, consisting of:
   (a) a cationic pest control active ingredient;
   (b) a nonionic thickening agent;
   (c) a nonionic surface active agent;
   (d) a solid active ingredient;
   (e) water;
   (f) an antifreezing agent that is at least one selected from the group consisting of ethylene glycol, ethyl diglycol, ethyl triglycol propylene glycol, dipropylene glycol, tripropylene glycol, diethylene glycol, butanediol, and butyl diglycol;
   (g) an antifoaming agent of polydimethylsiloxane; and
   (h) a preservative that is at least one selected from the group consisting of 1,2-benzisothiazolin-3-one, 5-chloro-2-methyl-4-isothiazolin-3-one, 2-methyl-4-

TABLE 2

| | Suspension Composition | Component (a) (parts by weight) | Component (b) (parts by weight) | Component (c) (parts by weight) | Component (d) (parts by weight) | Component (e) (parts by weight) | Supernatant separation rate (%) |
|---|---|---|---|---|---|---|---|
| Ex. 20 | 20 | 3 | 1.5 | 2 | 27.3 | 63.5 | 1 |
| Ex. 21 | 21 | 3 | 1.5 | 2 | 27.3 | 63.5 | 11 |
| Ex. 22 | 22 | 3 | 3.6 | 2 | 27.3 | 61.4 | 5 |
| Ex. 23 | 23 | 3 | 3.6 | 2 | 27.3 | 61.4 | 8 |
| Comp. Ex. 8 | 32 | 3 | — | 2 | 27.3 | 64.7 | 43 |
| Comp. Ex. 9 | 33 | 3 | — | 2 | 27.3 | 64.7 | 53 | isothiazolin-3-one, ascorbic acid, hexamethylenetetramine, sodium propionate, sorbic acid, a sulfurous acid solution-paraformaldehyde, benzoic acid, propyl p-hydroxybenzoate, methyl p-hydroxybenzoate, sodium benzoate, ascorbyl palmitate, and sodium 1,1'-biphenyl-2-olate; wherein:

the amount of the cationic pest control active ingredient is 5-50% by weight, with respect to the pest control agent as a whole, the cationic pest control active ingredient is at least one selected from the group consisting of iminoctadine albesilate and iminoctadine acetate, the nonionic thickening agent is at least one selected from the group consisting of cellulose derivative, pullulan, pectin, propylene glycol alginate, and guar gum, the nonionic surface active agent is at least one selected from the group consisting of a polyoxyalkylene alkyl ether, a polyoxyalkylene styryl phenyl ether, a polyoxyalkylene alkyl ester, a polyoxyalkylene sorbitan fatty acid ester, a polyoxyalkylene castor oil ether, a polyoxyethylene polyoxypropylene block polymer, and a polyoxyalkylene alkylamine, the solid active ingredient is a compound having a melting point of 40° C. or more and a solubility of 1% by weight or less in water at 25° C., the amount of the nonionic thickening agent is 0.1-5% by weight, with respect to the pest control agent as a whole, the amount of the nonionic surface active agent is 0.1-10% by weight, with respect to the pest control agent as a whole, and the amount of the solid active ingredient is 5-50% by weight, with respect to the pest control agent as a whole.

\* \* \* \* \*